US012144856B2

(12) United States Patent
Yuen et al.

(10) Patent No.: US 12,144,856 B2
(45) **Date of Patent: *Nov. 19, 2024**

(54) COMPOSITIONS AND METHODS FOR ENHANCING IMMUNE RESPONSE TO VACCINATION AND IMPROVING VACCINE PRODUCTION

(71) Applicant: Versitech Limited, Telegraph Bay (HK)

(72) Inventors: Kwok Yung Yuen, Pok Fu Lam (HK); Kai Wang Kelvin To, Pok Fu Lam (HK); Shuofeng Yuan, Kennedy Town (HK); Fuk Woo Jasper Chan, Kowloon (HK); Jinxia Zhang, Tai Po New Town (HK); Fan Ngai Hung, Mid-Level (HK); Johnson Yiu-Nam Lau, Houston, TX (US)

(73) Assignee: VERSITECH LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/738,692

(22) Filed: Jan. 9, 2020

(65) Prior Publication Data

US 2020/0215185 A1 Jul. 9, 2020

Related U.S. Application Data

(60) Provisional application No. 62/790,373, filed on Jan. 9, 2019.

(51) Int. Cl.

| | |
|---|---|
| ***A61K 39/145*** | (2006.01) |
| ***A61K 8/55*** | (2006.01) |
| ***A61K 9/00*** | (2006.01) |
| ***A61K 31/16*** | (2006.01) |
| ***A61K 31/685*** | (2006.01) |
| ***A61K 39/00*** | (2006.01) |
| ***A61K 39/215*** | (2006.01) |
| ***A61K 47/54*** | (2017.01) |
| ***C12N 7/00*** | (2006.01) |
| ***C12Q 1/70*** | (2006.01) |
| ***G01N 33/94*** | (2006.01) |

(52) U.S. Cl.

CPC ............ *A61K 39/145* (2013.01); *A61K 8/553* (2013.01); *A61K 9/0014* (2013.01); *A61K 31/16* (2013.01); *A61K 31/685* (2013.01); *A61K 39/215* (2013.01); *A61K 47/544* (2017.08); *C12N 7/00* (2013.01); *C12Q 1/70* (2013.01); *G01N 33/948* (2013.01); *A61K 2039/55511* (2013.01); *C12N 2760/16034* (2013.01); *C12N 2770/20034* (2013.01)

(58) Field of Classification Search

CPC .... A61K 2300/00; A61K 39/12; A61K 39/39; A61K 39/00; A61K 39/145; A61K 48/0075; A61K 2039/54; A61K 31/713; A61K 2039/5252; A61K 31/4745; A61K 9/0014; A61K 45/06; A61K 2039/55566; A61K 2039/575; A61K 2039/55511; A61K 2039/545; A61P 31/16; C12N 7/00; C12N 15/86; C12N 2760/16034; C12N 2760/16234; C12N 2760/16134; C07K 14/005; C07K 16/1018; C07K 2317/76; C07K 2317/34; C07D 519/00

See application file for complete search history.

(56) References Cited

U.S. PATENT DOCUMENTS

2007/0224224 A1 9/2007 Cordeira Da Silva et al.
2010/0055670 A1 3/2010 Kaplan et al.
2010/0158947 A1 6/2010 Delputte et al.

FOREIGN PATENT DOCUMENTS

WO WO-2010122310 A2 10/2010
WO WO-2011006219 A1 1/2011

OTHER PUBLICATIONS

Sunyoto T, Potet J, Boelaert M. Why miltefosine—a life-saving drug for leishmaniasis—is unavailable to people who need it the most. BMJ Glob Health. May 3, 2018;3(3):e000709. (Year: 2018).*

Sinkala E, Katubulushi M, Sianongo S, Obwaller A, Kelly P. In a trial of the use of miltefosine to treat HIV-related cryptosporidiosis in Zambian adults, extreme metabolic disturbances contribute to high mortality. Ann Trop Med Parasitol. Mar. 2011;105(2):129-34. (Year: 2011).*

Mukherjee AK, Gupta G, Adhikari A, Majumder S, Kar Mahapatra S, Bhattacharyya Majumdar S, Majumdar S. Miltefosine triggers a strong proinflammatory cytokine response during visceral leishmaniasis: role of TLR4 and TLR9. Int Immunopharmacol. Apr. 2012; 12(4):565-72. Epub Feb. 21, 2012. (Year: 2012).*

Dowling DJ. Immunohorizons. Jul. 2, 2018;2(6):185-197. (Year: 2018).*

Vasilakos JP, et. al. Expert Rev Vaccines. Jul. 2013;12(7):809-19. (Year: 2013).*

Engel AL, et. al. Expert Rev Clin Pharmacol. Mar. 2011;4(2):275-89. (Year: 2011).*

Kigasawa K, et. al. J Control Release. Mar. 30, 2011;150(3):256-65. Epub Jan. 21, 2011. (Year: 2011).*

Dorlo TP, Balasegaram M, Beijnen JH, de Vries PJ. Miltefosine: a review of its pharmacology and therapeutic efficacy in the treatment of leishmaniasis. J Antimicrob Chemother. Nov. 2012;67(11):2576-97. Epub Jul. 24, 2012. (Year: 2012).*

(Continued)

*Primary Examiner* — Rachel B Gill

(74) *Attorney, Agent, or Firm* — PABST PATENT GROUP LLP

(57) ABSTRACT

Miltefosine is utilized to enhance immune response to vaccination, for example an influenza and/or coronavirus vaccination. The inventive subject matter also provides compositions and methods for enhancing viral yield in cultured cells, by application of a cannabinoid receptor agonist (such as methanandamide) to such cells. Such enhanced viral yield can be used to enhance virus production for purposes of vaccine formulation and/or to improve sensitivity of cell-based virus assays.

15 Claims, 5 Drawing Sheets

(56) References Cited

OTHER PUBLICATIONS

Gerdts V, Zakhartchouk A. Vaccines for porcine epidemic diarrhea virus and other swine coronaviruses. Vet Microbiol. Jul. 2017;206:45-51. Epub Dec. 2, 2016. (Year: 2016).*
Belongia EA, Simpson MD, King JP, Sundaram ME, Kelley NS, Osterholm MT, McLean HQ. Variable influenza vaccine effectiveness by subtype: a systematic review and meta-analysis of test-negative design studies. Lancet Infect Dis. Aug. 2016;16(8):942-51. Epub Apr. 6, 2016. (Year: 2016).*
Pulendran B, S Arunachalam P, O'Hagan DT. Emerging concepts in the science of vaccine adjuvants. Nat Rev Drug Discov. Jun. 2021;20(6):454-475. Epub Apr. 6, 2021. (Year: 2021).*
Offit PA. Children's Hospital of Philadelphia (CHOP). Antibody-dependent Enhancement (ADE) and Vaccines. Sep. 9, 2021. https://www.chop.edu/centers-programs/vaccine-education-center/vaccine-safety/antibody-dependent-enhancement-and-vaccines). (Year: 2021).*
Gupta RK, Siber GR. Adjuvants for human vaccines—current status, problems and future prospects. Vaccine. Oct. 1995;13(14):1263-76. (Year: 1995).*
Petrovsky N. Comparative Safety of Vaccine Adjuvants: A Summary of Current Evidence and Future Needs. Drug Saf. Nov. 2015;38(11):1059-74. (Year: 2015).*
Peralta MF, Usseglio NA, Bracamonte ME, Guzmán ML, Olivera ME, Marco JD, Barroso PA, Carrer DC. Efficacy of topical Miltefosine formulations in an experimental model of cutaneous leishmaniasis. Drug Deliv Transl Res. Jan. 2022;12(1):180-196. Epub Jan. 27, 2021. (Year: 2021).*
Ware JM, O'Connell EM, Brown T, Wetzler L, Talaat KR, Nutman TB, Nash TE. Efficacy and Tolerability of Miltefosine in the Treatment of Cutaneous Leishmaniasis. Clin Infect Dis. Oct. 5, 2021;73(7):e2457-e2562. (Year: 2021).*
Belongia, E.A., et al., "Variable Influenza Vaccine Effectiveness by Subtype: a Systematic Review and Meta-analysis of Test-negative Design Studies," Lancet Infectious Diseases, Aug. 2016, vol. 16 (8), pp. 942-951.
Black, S., et al., "Safety of MF59-adjuvanted Versus Non-adjuvanted Influenza Vaccines in Children and Adolescents: an Integrated Analysis," Vaccine, Oct. 2010, vol. 28(45), pp. 7331-7336.
CDC Health Advisory Regarding the Potential for Circulation of Drifted Influenza A (H3N2) Viruses, CDC Health Advisory, Distributed via the CDC Health Alert Network, Dec. 3, 2014, 7 pages.
Centers for Disease Control and Prevention, MMWR, "Prevention and Control of Seasonal Influenza with Vaccines: Recommendations of the Advisory Committee on Immunization Practices—United States, 2018-19 Influenza Season," Recommendations and Reports / vol. 67 / No. 3, Morbidity and Mortality Weekly Report, Aug. 24, 2018, U.S. Department of Health and Human Services, 24 pages.
Clive S., et al., "Miltefosine as a topical treatment for cutaneous metastases in breast carcinoma," Cancer Chemotherapy and Pharmacology, 1999, vol. 44, pp. Suppl:S29-S30.
Das, S., et al., "Combination of Paromomycin and Miltefosine Promotes TLR4-dependent Induction of Antileishmanial Immune Response in Vitro," Journal of Antimicrobial Chemotherapy, Oct. 2012, vol. 67(10), pp. 2373-2378.
Gutjahr A., et al., "Triggering Intracellular Receptors for Vaccine Adjuvantation," Trends in Immunology, Sep. 2016, vol. 37(9), pp. 573-587.
Hung, I.F.N., et al., "Dose Sparing Intradermal Trivalent Influenza (2010/2011) Vaccination Overcomes Reduced Immunogenicity of the 2009 H1N1 Strain," Vaccine, Oct. 2012, vol. 30 (45), pp. 6427-6435.
Hung I.F.N., et al., "Immunogenicity of Intradermal Trivalent Influenza Vaccine With Topical Imiquimod: a Double Blind Randomized Controlled Trial," Clinical Infectious Diseases, Nov. 2014, vol. 59(9), pp. 1246-1255.
Hung, I.F-N., et al.. "Topical Imiquimod Before Intradermal Trivalent Influenza Vaccine for Protection Against Heterologous Non-vaccine and Antigenically Drifted Viruses: A Single-centre, Double-blind, Randomised, Controlled Phase 2b/3 Trial", Lancet Infectious Disease, 2016, vol. 16, pp. 209-218.
International Search Report for PCT Application No. PCT/US2020/012885, mailed on May 7, 2020, 4 pages.
Kanekiyo M., et al., "Self-assembling Influenza Nanoparticle Vaccines Elicit Broadly Neutralizing H1N1 Antibodies," Nature, Jul. 2013, vol. 499 (7456), pp. 102-106.
Levitz, S.M., et al., "Beyond Empiricism: Informing Vaccine Development Through Innate Immunity Research," Cell, Mar. 2012, vol. 148(6), pp. 1284-1292.
Li, C., et al., "Co-stimulation With TLR7 Agonist Imiquimod and Inactivated Influenza Virus Particles Promotes Mouse B Cell Activation, Differentiation, and Accelerated Antigen Specific Antibody Production," Frontiers in Immunology, 2018, vol. 9, pp. 2370.
Lucas, A., et al., "Targeting the PI3K/Akt Cell Survival Pathway to Induce Cell Death of HIV-1 Infected Macrophages with Alkylphospholipid Compounds," PLoS One, 2010, vol. 5 (9), pp. e13121.
Montana, M., et al., "Safety Review: Squalene and Thimerosal in Vaccines," Therapies, Nov.-Dec. 2010, vol. 65 (6), pp. 533-541.
Mukherjee, A.K., et al., "Miltefosine Triggers a Strong Proinflammatory Cytokine Response During Visceral Leishmaniasis: Role of TLR4 and TLR9," International Immunopharmacology, Apr. 2012, vol. 12(4), pp. 565-572.
Pearton, M., et al., "Changes in Human Langerhans Cells Following Intradermal Injection of Influenza Virus-Like Particle Vaccines," PLoS One, 2010, vol. 5(8), pp. e12410.
Saxena M., et al., "Turbocharging Vaccines: Emerging Adjuvants for Dendritic Cell Based Therapeutic Cancer Vaccines," Current Opinion in Immunology, Aug. 2017, vol. 47, pp. 35-43.
Skowronski, D.M., et al., "Interim Estimates Of 2014/15 Vaccine Effectiveness Against Influenza A(H3N2) from Canada's Sentinel Physician Surveillance Network, Jan. 2015," Eurosurveillance, Jan. 2015, vol. 20(4), pp. 21022.
Thomsen, L.L., et al., "Imiquimod and Resiquimod in a Mouse Model: Adjuvants for DNA Vaccination by Particle-mediated Immunotherapeutic Delivery," Vaccine, Apr. 2004, vol. 22 (13-14), pp. 1799-1809.
To, K.K.W., et al., "Recombinant Influenza a Virus Hemagglutinin HA2 Subunit Protects Mice Against Influenza A(H7N9) Virus Infection," Archives of Virology, Mar. 2015, vol. 160(3), pp. 777-786.
Tregoning, J.S., et al., "Adjuvanted Influenza Vaccines," Human Vaccines & Immunotherapeutics, 2018, vol. 14 (3), pp. 550-564.
Vaccine Effectiveness: How Well Do the Flu Vaccines Work?, Influenza (Flu), Centers for Disease and Control Prevention, 2020, 7 pages.
Vesikari, T., et al., "Efficacy, Immunogenicity, and Safety Evaluation of an Mf59-adjuvanted Quadrivalent Influenza Virus Vaccine Compared With Non-adjuvanted Influenza Vaccine in Children: a Multicentre, Randomised Controlled, Observer-blinded, Phase 3 Trial," Lancet Respiratory Medicine, May 2018, vol. 6 (5), pp. 345-356.
Wadhone, P., et al., "Miltefosine Promotes IFN-γ-dominated Anti-leishmanial Immune Response," Journal of Immunology, Jun. 2009, vol. 182(11), pp. 7146-7154.
Weldon, W.C., et al., "Effect of Adjuvants on Responses to Skin Immunization by Microneedles Coated with Influenza Subunit Vaccine," PLoS One, 2012, vol. 7(7), pp. e41501.
Zhang, A.J.X., et al., "Toll-Like Receptor 7 Agonist Imiquimod in Combination with Influenza Vaccine Expedites and Augments Humoral Immune Responses against Influenza A(H1N1)PDM09 Virus Infection in BALB/C Mice," Clinical and Vaccine Immunology, Apr. 2014, vol. 21 (4), pp. 570-579.
Zimmerman,R.K., et al., "2014-2015 Influenza Vaccine Effectiveness in the United States by Vaccine Type," Clinical Infectious Diseases, Dec. 2016, vol. 63 (12), pp. 1564-1573.
Zuber A.K., et al., "Topical Delivery of Imiquimod to a Mouse Model as a Novel Adjuvant for Human Immunodeficiency Virus (HIV) DNA," Vaccine, Apr. 2004, vol. 22 (113-14), pp. 1791-1798.

* cited by examiner

COMPOSITIONS AND METHODS FOR ENHANCING IMMUNE RESPONSE TO VACCINATION AND IMPROVING VACCINE PRODUCTION

This application claims the benefit of U.S. Provisional Application No. 62/790,373 filed on Jan. 9, 2019. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is viral vaccine formulations and adjuvants for use with vaccine formulations.

BACKGROUND

The background description includes information that may be useful in understanding the present invention. It is not an admission that any of the information provided herein is prior art or relevant to the presently claimed invention, or that any publication specifically or implicitly referenced is prior art. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Influenza poses a heavy burden to our health service (Centers for Disease Control and Prevention. Vaccine Effectiveness-How Well Does the Flu Vaccine Work? Available at web page cdc.gov/flu/about/qa/vaccineeffect.htm. Accessed on Dec. 8, 2018; Belongia E A, Simpson M D, King J P, Sundaram M E, Kelley N S, Osterholm M T, et al. Variable influenza vaccine effectiveness by subtype: a systematic review and meta-analysis of test-negative design studies. Lancet Infect Dis 2016; 16:942-51), causing significant morbidity and mortality in older people, very young children and persons with chronic illness. Seasonal, zoonotic and pandemic influenza are constant global threats. The World Health Organization estimates that seasonal influenza causes 250,000-500,000 deaths worldwide each year. Most recently, the antigenically drifted A/Switzerland/9715293/2013 virus caused major outbreaks in various countries in Europe and North America (CDC Health Advisory regarding the potential for circulation of drifted influenza A (H3N2) viruses internet site emergency.cdc.gov/HAN/han00374.asp; Skowronski D M, Drews S J, Fonseca K, Charest H, Chambers C, Sabaiduc S, et al. Interim estimates of 2014/5 vaccine effectiveness against influenza A (H3N2) from Canada's sentinel physician surveillance network. Euro Surveill 2015;20. Pi: 21022). Virological surveillance of influenza A(H3N2) viruses collected in the United States from October 1 through Nov. 22, 2014 showed that 52% of these isolates were antigenically drifted from the A/Texas/50/2012(H3N2) vaccine virus (Grohskopf L A, Sokolow L Z, Broder K R, Walter E B, Fry A M, Jernigan D B. Prevention and Control of Seasonal Influenza with Vaccines: Recommendations of the Advisory Committee on Immunization Practices-United States, 2018-19 Influenza Season. MMWR Recomm Rep 2018; 67:1-20). Moreover, avian influenza viruses such as the A(H5N1) and more recently A(H7N9), the spread of which from their regions of origin is facilitated by air travel, are often associated with a much higher mortality than traditional seasonal influenza. As such, the protective potential of immunizing formulations based on predictions of likely pathogenic strains made well in advance of actual outbreaks is necessarily limited.

One approach to addressing this problem is to increase the complexity of the vaccinating formulation. For example, co-circulation of Influenza B Yamagata and Victoria strains leading to seasonal outbreaks resulted in a call for the routine use of a quadrivalent influenza vaccine. Such an approach, however, further complicates production of seasonal influenza vaccines and does not address the fundamental issue of genetic drift from predicted strains and unanticipated introduction of new influenza strains.

Imiquimod, a synthetic toll-like receptor 7 (TLR7) agonist useful for the treatment of DNA virus infection, has been found to improve certain aspects of influenza vaccine immunogenicity in experimental animal models (Thomsen L L, Topley P, Daly M G, Brett S J, Tite J P. Imiquimod and resiquimod in a mouse model: adjuvants for DNA vaccination by particle-mediated immunotherapeutic delivery. Vaccine. 2004; 22:1799-809; Zuber A K, Brave A, Engstrom G, Zuber B, Ljungberg K, Fredriksson M, et al. Topical delivery of imiquimod to a mouse model as a novel adjuvant for human immunodeficiency virus (HIV) DNA. Vaccine. 2004; 22:1791-8; Weldon W C, Zarnitsyn V G, Esser E S, Taherbhai M T, Koutsonanos D G, Vassilieva E V, et al. Effect of adjuvants on responses to skin immunization by microneedles coated with influenza subunit vaccine. PLoS One. 2012; 7: e41501; Zhang A J, Li C, To K K, Zhu H S, Lee A C, Li C G, et al. Toll-like receptor 7 agonist imiquimod in combination with influenza vaccine expedites and augments humoral immune responses against influenza A(H1N1)pdm09 virus infection in BALB/c mice. Clin Vaccine Immunol. 2014; 21:570-9). For example, treatment with topical imiquimod before intradermal trivalent influenza vaccine expedited, augmented and prolonged the immunogenicity against the immunizing influenza vaccine strains in elderly subjects with chronic illness (Hung I F, Zhang A J, To K K, Chan J F, Li C, Zhu H S, et al. Immunogenicity of intradermal trivalent influenza vaccine with topical imiquimod: a double blind randomized controlled trial. Clin Infect Dis 2014; 59:1246-55). Similar studies have noted a boost in immune response to vaccinating species as an effect of a topical TLR7 agonist, imiquimod in both human and animal models. The immunity induced was rapid and could sustain beyond the one-year period in immunosenescent elderly subjects. An imiquimod adjuvanted (i.e. mixed and injected with the vaccine formulation) vaccine has also been found to elicit higher level of IgG2a antibodies, HI titers and IFN-γ cellular response directed to immunizing species when compared to vaccine alone. Simultaneous subcutaneous administration of imiquimod as an adjuvant with DNA vaccine also enhanced the dendritic cell and Th1 lymphocyte response towards the injected antigens in mouse model (Thomsen L L, Topley P, Daly M G, Brett S J, Tite J P. Imiquimod and resiquimod in a mouse model: adjuvants for DNA vaccination by particle-mediated immunotherapeutic delivery. Vaccine. 2004; 22:1799-809; Zuber A K, Brave A, Engstrom G, Zuber B, Ljungberg K, Fredriksson M, et al. Topical delivery of imiquimod to a mouse model as a novel adjuvant for human immunodeficiency virus (HIV) DNA. Vaccine. 2004; 22:1791-8). Such an increased response to vaccinated species, however, does not address issues resulting from antigenic drift or introduction of new influenza virus strains that are not present in a vaccinating formulation to a population.

Other strategies have been studied to improve the immunogenicity and breadth of the influenza vaccine by targeting the relatively conserved hemagglutinin stem, the M2 and the nucleoprotein, or by changing the mode of delivery with viral vectors. More recently, the development of self-assembling synthetic nanoparticle vaccine was also found to improve the potency and breadth of influenza virus immunity (Kanekiyo M, Wei C J, Yassine H M, McTamney P M, Boyington J C, Whittle J R, et al. Self-assembling influenza nanoparticle vaccines elicit broadly neutralizing H1N1 antibodies. Nature 2013; 499:102-6). Nevertheless, such strategies are still confined to the stage of cell-line or animal studies. The use of adjuvants including the MF59 or AS03 has demonstrated an antigen sparing effect with improved immunogenicity. Unfortunately, ] frequent local adverse events limit its utility (Montana M, Verhaeghe P, Ducros C, Terme T, Vanelle P, Rathelot P. Safety review: squalene and thimerosal in vaccines. Therapie 2010; 65:533-41; Black S, Della Cioppa G, Malfroot A, Nacci P, Nicolay U, Pellegrini M, et al. Safety of MF59-adjuvanted versus non-adjuvanted influenza vaccines in children and adolescents: an integrated analysis. Vaccine 2010; 28:7331-6). In addition, the dose sparing effect is less pronounced in individuals who have been primed earlier in their lives with antigenically related viruses or vaccines. Therefore, the application of topical imiquimod pretreatment before intradermal influenza vaccination is the most simple and readily available strategy to improve and broaden the influenza vaccine immunogenicity. It has also been noted that the combination of synthetic TLR4 and TLR7 ligands can act as an adjuvant when coinjected with recombinant influenza virus hemagglutinin, and can stimulate both Th1 and Th2-type immune responses in mice, thereby providing broad neutralizing antibodies against the antigenically drifted influenza viruses (Mukherjee A K, Gupta G, Adhikari A, Majumder S, Kar Mahapatra S, Bhattacharyya Majumdar S, et al. Miltefosine triggers a strong proinflammatory cytokine response during visceral leishmaniasis: role of TLR4 and TLR9. Int Immunopharmacol 2012; 12:565-72). It is not clear, however, how effective such approaches will be in widespread immunization efforts.

Thus, there is still a need for a simple, effective, and well tolerated compositions and methods that provide an enhanced immune response and/or broadened range of effective responses to vaccine formulations.

SUMMARY OF THE INVENTION

The inventive subject matter provides compositions and methods in which miltefosine is utilized to enhance immune response (for example, as an adjuvant) to vaccination (e.g. an influenza and/or coronavirus vaccination). The inventive subject matter also provides compositions and methods for enhancing viral yield in cultured cells, by application of a cannabinoid receptor agonist (such as methanandamide) to such cells. Such enhanced viral yield can be used to enhance virus production for purposes of vaccine formulation and/or to improve sensitivity of cell-based virus assays.

One embodiment of the inventive concept is a method for improving an immune response to vaccination by providing an adjuvant that includes miltefosine (e.g. 1 μg to 100 mg of miltefosine) to a subject at or immediately prior to vaccination, and introducing a vaccine (which includes a vaccinating species) at a vaccination site. The adjuvant can be provided as a topical formulation that is selected to provide miltefosine in a quantity sufficient to enhance an immune response to the vaccinating species. Examples of such immune responses include IgG titer, IgM titer, hemagglutination inhibition titer, and microneutralization titer. When the adjuvant is formulated as a topical formulation, a barrier can be applied over the site where the topical formulation is applied (e.g. the vaccination site). Such a topical formulation can be provided as part of an application device. The method can be applied to immunization with trivalent influenza vaccine, multivalent influenza vaccine, and/or a coronavirus vaccine.

Another embodiment of the inventive concept is the use of miltefosine in the preparation of an adjuvant that provides an enhanced response to a vaccine (e.g. trivalent influenza vaccine, multivalent influenza vaccine, and/or a coronavirus vaccine). Such an adjuvant can be formulated to provide between 1 μg and 100 mg of miltefosine, and can be provided as part of an appliance. Enhanced responses include but are not limited to increased IgG titer, increased IgM titer, increased hemagglutination inhibition titer, and increased microneutralization titer, relative to vaccination response achieved in a vaccinated subject that has not been treated with the adjuvant.

Another embodiment of the inventive concept is an adjuvant for enhancing an immune response to an intradermally injected vaccine (trivalent influenza vaccine, multivalent influenza vaccine, or a coronavirus vaccine), which includes miltefosine. The immune response includes but is not limited to IgG titer, IgM titer, hemagglutination inhibition titer, and/or microneutralization titer. Such an adjuvant can provide from 1 μg to 100 mg of miltefosine, and in some embodiments can be formulated for topical application. Such a topical formulation can be part of an application device.

Another embodiment of the inventive concept is a vaccine formulation (e.g. trivalent influenza vaccine, multivalent influenza vaccine, and/or a coronavirus vaccine) for providing a therapeutic or protective immunity, which includes an immunogenic vaccinating species and miltefosine. The vaccine formulation can include 1 μg to 100 mg of t miltefosine.

Another embodiment of the inventive concept is a method of increasing yield of a virus from cell culture by contacting a cell in culture with genetic material from the virus, and also contacting the cell with a cannabinoid receptor agonist (e.g. (R)-methanandamide) at a non-toxic concentration. The cannabinoid receptor agonist is selected to increase lipid content of the cell. The virus or a portion thereof can be suitable for use as an immunogen (e.g. a coronavirus or an influenza virus).

Another embodiment of the inventive concept is method of producing a vaccine formulation by contacting a cell in culture with genetic material from a virus (e.g. a coronavirus and/or an influenza virus), contacting the cell with a cannabinoid receptor agonist selected to increase lipid content of the cell (e.g. (R)-methanandamide) at a non-toxic concentration, collecting virus from the culture following a period of time sufficient for replication of the virus in the cell, and providing the virus or a portion of the virus in a pharmaceutically acceptable carrier. The virus or a portion thereof is suitable for use as an immunogen. In some embodiments miltefosine is added to the pharmaceutically acceptable carrier.

Another embodiment of the inventive concept is a method for detecting a virus (e.g. a coronavirus or an influenza virus) by obtaining a sample suspected of containing the virus, contacting a cell in culture with at least a portion of the sample or a fraction derived from the sample, contacting the cell with a cannabinoid receptor agonist selected to increase lipid content of the cell at a non-toxic concentration, collecting a test sample from the culture following a period of time sufficient for replication of the virus in the cell, and determining the presence of a molecule characteristic of the virus in the test sample (e.g. by nucleic acid amplification, nucleic acid hybridization, and/or immunoassay). The period of time sufficient for replication of the virus in the cell can be prior to observation of cytopathic effects. In some embodiments determining the presence of the molecule characteristic of the virus is performed using a rapid or point of care test.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 depicts antibody titers measured 14 days after vaccination with or without miltefosine. A second dose of vaccine was provided on day 14. Circles indicate data from the miltefosine+vaccine treatment group; squares indicate data from the vaccine only treatment group; triangles indicate data from the miltefosine only treatment group; inverted triangles indicate data from a saline-treated control group.

FIG. 2A depicts survival rates of infected mice that were vaccinated with or without miltefosine 3 days prior to infection. Data from treatment with 0.2 mg miltefosine+vaccine is represented by a combination a circle and a solid line. Data from treatment with 0.008 mg miltefosine+vaccine is represented by a combination of a rhombus and a dashed line. Data from treatment with 0.2 mg miltefosine only is represented by a dash/dot line. Data from treatment with vaccine only is represented by a combination of a square and a solid line. Data from treatment with a saline control is represented by a dotted line. FIG. 2B depicts survival rates of infected mice that were vaccinated with (circle/dashed line, rhombus/dashed line, or black) or without (square/solid line) miltefosine 7 days prior to infection. Data from treatment with 1 mg miltefosine+vaccine is represented by a combination a triangle and a solid line. Data from treatment with 0.2 mg miltefosine+vaccine is represented by a combination a circle and a solid line. Data from treatment with 0.008 mg miltefosine+vaccine is represented by a combination of a rhombus and a dashed line. Data from treatment with 0.2 mg miltefosine only is represented by a dash/dot line. Data from treatment with vaccine only is represented by a combination of a square and a solid line. Data from treatment with a saline control is represented by a dotted line.

FIG. 3 depicts two, four or six days post-infection antibody, hemagglutination, and microneutralization titers of infected mice that were vaccinated with or without an intraperitoneal miltefosine adjuvant three days before infection. Circles indicate data from the miltefosine+vaccine treatment group; squares indicate data from the vaccine only treatment group; triangles indicate data from the miltefosine only treatment group; inverted triangles indicate data from a saline-treated control group.

FIG. 4 depicts the percentage of splenic follicular T cells of infected mice that had been vaccinated with or without an intraperitoneal miltefosine adjuvant seven days prior to infection on day 7. Data shown represents findings on day 7 (i.e. seven days after treatment with miltefosine and vaccine) but prior to infection (left side) and two days after infection (day 9, right side).

FIG. 5 depicts the structure of and exemplary cannabinoid receptor agonist, (R)-methanandamide.

FIG. 6 depicts results of viral cytopathic effect studies in the presence and absence of (R)-methanandamide

DETAILED DESCRIPTION

Figure 1:
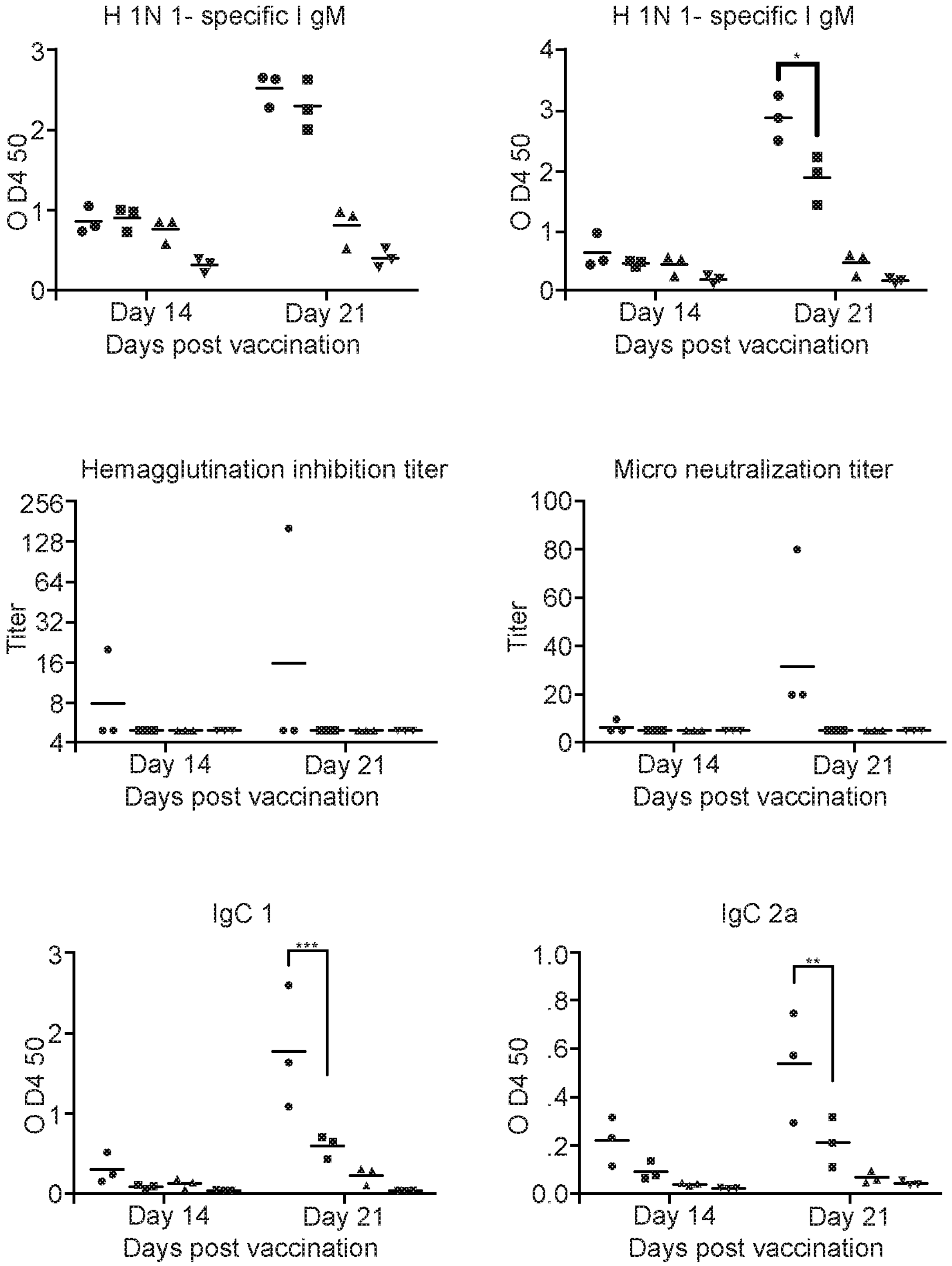
FIG. 1.

The following description includes information that may be useful in understanding the present invention. It is not an admission that any of the information provided herein is prior art or relevant to the presently claimed invention, or that any publication specifically or implicitly referenced is prior art.

Overall influenza vaccine effectiveness is only about 40-60% (Centers for Disease Control and Prevention. Vaccine Effectiveness—How Well Does the Flu Vaccine Work? Available at web page cdc.gov/flu/about/qa/vaccineeffect.htm. Accessed on Dec. 8, 2018). The effectiveness for influenza A(H3N2) is particularly poor, with a pooled vaccine effectiveness of only <35% (Belongia E A, Simpson M D, King J P, Sundaram M E, Kelley N S, Osterholm M T, et al. Variable influenza vaccine effectiveness by subtype: a systematic review and meta-analysis of test-negative design studies. Lancet Infect Dis 2016; 16:942-51). Vaccine effectiveness is also lower when there is a major mutation in the virus. For example, in the 2014-2015 influenza season which is dominated by an antigenically-drifted A(H3N2) virus, the vaccine effectiveness was only 19% (Zimmerman R K, Nowalk M P, Chung J, Jackson M L, Jackson L A, Petrie J G, et al. 2014-2015 Influenza Vaccine Effectiveness in the United States by Vaccine Type. Clin Infect Dis 2016; 63:1564-73).

In order to improve vaccine effectiveness, adjuvants have been incorporated into vaccine preparations. The only commercially-available adjuvanted vaccine for seasonal influenza, Fluad™ (Seqirus), contains MF59, which is a squalene-based emulsion (Grohskopf L A, Sokolow L Z, Broder K R, Walter E B, Fry A M, Jernigan D B. Prevention and Control of Seasonal Influenza with Vaccines: Recommendations of the Advisory Committee on Immunization Practices-United States, 2018-19 Influenza Season. MMWR Recomm Rep 2018; 67:1-20). However, the effectiveness of MF59-adjuvanted vaccine is only superior to that of non-adjuvanted vaccine for specific age groups (Vesikari T, Kirstein J, Devota Go G, Leav B, Ruzycky M E, Isakov L, et al. Efficacy, immunogenicity, and safety evaluation of an MF59-adjuvanted quadrivalent influenza virus vaccine compared with non-adjuvanted influenza vaccine in children: a multicentre, randomised controlled, observer-blinded, phase 3 trial. The lancet Respiratory medicine 2018; 6:345-56). The hemagglutination titer with MF59-adjuvanted influenza vaccine is only 1.14-1.4-fold higher than that of non-adjuvanted vaccine (Tregoning J S, Russell R F, Kinnear E. Adjuvanted influenza vaccines. Hum Vaccin Immunother 2018; 14:550-64).

Advances in understanding of the molecular mechanism of innate immunity in the past decade have paved the way for developing novel and chemically-defined adjuvants that activate different receptors and sensors such as Toll-like receptors (TLRs) and RIG-I-like receptors (RLRs) (Levitz S M, Golenbock D T. Beyond empiricism: informing vaccine development through innate immunity research. Cell 2012; 148:1284-92). Several TLR agonists have now been licensed for human use or are in late phases of clinical trials (Saxena M, Bhardwaj N. Turbocharging vaccines: emerging adjuvants for dendritic cell based therapeutic cancer vaccines. Curr Opin Immunol 2017; 47:35-43). In addition to TLRs, RLRs are another group of important sensors in innate immunity that detect viral nucleic acids in the cytoplasm. In contrast to TLRs that are expressed in immune cells, RLRs are ubiquitous. Binding of RLR to agonists generates an activation signal which leads to the production of type I interferons (IFNs). Therefore, RLR agonists are excellent candidates of vaccine adjuvants (Gutjahr A, Tiraby G, Perouzel E, Verrier B, Paul S. Triggering Intracellular Receptors for Vaccine Adjuvantation. Trends Immunol 2016; 37:716). They can serve as "built-in" adjuvants in attenuated and DNA vaccines.

The Inventors have been actively pursuing novel adjuvants that activate native receptors and sensors. One approach is to use an adjuvant to accelerate and augment the immune response by intradermal influenza vaccine. Traditionally, influenza vaccines are given via the intramuscular route. However, it has been shown that a much stronger (and potentially more effective) antibody response can be induced via intradermal administration of the influenza vaccine (Hung I F, Levin Y, To K K, Chan K H, Zhang A J, Li P, et al. Dose sparing intradermal trivalent influenza (2010/2011) vaccination overcomes reduced immunogenicity of the 2009 H1N1 strain. Vaccine 2012; 30:6427-35). Without wishing to be bound by theory, it is theorized that the improved response conferred by intradermal vaccination can be primarily attributed to the involvement of an enhanced Langerhans cell response (Pearton M, Kang S M, Song J M, Anstey A V, Ivory M, Compans R W, et al. Changes in human Langerhans cells following intradermal injection of influenza virus-like particle vaccines. PLoS One 2010; 5: e12410).

To further improve and/or enhance the immunogenicity of intradermal vaccine an adjuvant that enhances dermal immune cells is required. Such an adjuvant can be provided by any suitable route, including intraperitoneal injection, subcutaneous or intradermal injection, intramuscular injection, oral ingestion, inhalation, and/or topical application to skin and/or mucus membranes. One such adjuvant identified by the Inventors is imiquimod, which is a commercially available FDA-approved TLR7 agonist. In a mouse model, it was demonstrated that imiquimod can accelerate and augment the immunogenicity of the influenza vaccine and that this improved immunogenicity was associated with a reduction in death during lethal challenge experiments performed using 2009 pandemic influenza A(H1N1) virus and avian influenza virus A(H7N9) (Zhang A J, Li C, To K K, Zhu H S, Lee A C, Li C G, et al. Toll-like receptor 7 agonist imiquimod in combination with influenza vaccine expedites and augments humoral immune responses against influenza A(H1N1)pdm09 virus infection in BALB/c mice. Clin Vaccine Immunol 2014; 21:570-9; To K K, Zhang A J, Chan A S, Li C, Cal J P, Lau C C, et al. Recombinant influenza A virus hemagglutinin HA2 subunit protects mice against influenza A(H7N9) virus infection. Arch Virol 2015; 160: 777-86). It was found that imiquimod improves the immunogenicity of influenza vaccine by directly promoting the activation and differentiation of B cells (Li C, To K K W, Zhang A J X, Lee A C Y, Zhu H, Mak W W N, et al. Co-stimulation With TLR7 Agonist Imiquimod and Inactivated Influenza Virus Particles Promotes Mouse B Cell Activation, Differentiation, and Accelerated Antigen Specific Antibody Production. Front Immunol 2018; 9:2370). Based on the promising results of these animal studies, two placebo-controlled randomized controlled human studies were performed to evaluate the use of topical imiquimod with influenza vaccine. The first trial was conducted with older adults. It was found that participants who received topical treatment with imiquimod prior to intradermal injection of influenza vaccine had both a more rapid and robust antibody response and a significantly lower rate of hospitalization and pneumonia compared to subjects treated with a sham topical aqueous cream before influenza vaccine (Hung I F, Zhang A J, To K K, Chan J F, Li C, Zhu H S, et al. Immunogenicity of intradermal trivalent influenza vaccine with topical imiquimod: a double blind randomized controlled trial. Clin Infect Dis 2014; 59:1246-55). The second trial was conducted using young adults. Participants in the topical imiquimod treatment group not only had faster and more robust antibody responses than those in the control group (sham aqueous cream) for homologous virus, but surprisingly also developed a much more robust antibody response against antigenically distinct viruses from the past and recently antigenically-drifted viruses that were not included in the vaccine formulation used (Hung I F, Zhang A J, To K K, Chan J F, Li P, Wong T L, et al. Topical imiquimod before intradermal trivalent influenza vaccine for protection against heterologous non-vaccine and antigenically drifted viruses: a single-centre, double-blind, randomised, controlled phase 2b/3 trial. Lancet Infect Dis 2016; 16:209-18). These findings have led to Inventors pursuing the use of other agents, including FDA approved topical drugs and vaccine virus components as an adjuvant for influenza vaccine.

The inventive subject matter provides compositions and methods in which miltefosine is utilized as an adjuvant that can be provided to a subject prior to, essentially simultaneously (e.g. within five minutes) with, of following vaccination, for example an intradermal influenza vaccination. Suitable vaccines include but are not limited to trivalent influenza vaccine, multivalent influenza vaccine, and/or a coronavirus vaccine. Such vaccinations can be intradermal and/or intramuscular. In a preferred embodiment of the inventive concept miltefosine is provided in a pharmaceutically acceptable carrier, and/or as part of a vaccine formulation.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

As noted above, in embodiments of the inventive concept miltefosine can provided to a candidate for immunization by any suitable means. For example, miltefosine can be injected into the peritoneal cavity in a pharmaceutically acceptable carrier. Alternatively, miltefosine can be injected into a layer of the skin and/or intramuscularly. In some embodiments miltefosine can be provided in a suspension or solution suitable for inhalation, for example for absorption via nasal and/or pulmonary membranes. Alternatively, in some embodiments miltefosine can be delivered to the subject via the oral, vaginal, or gastrointestinal mucosa.

In other embodiments miltefosine can be provided as a topical formulation that can be applied to the skin surface, for example at or near (e.g. within 10 cm) of the site of a vaccine injection. An example of such a formulation is Mitlex™, which contains 6% miltefosine and is approved for human use. In such embodiments miltefosine is applied to the skin of the injections site and/or the surrounding area.

Such application can provide from up to 1 μg, 5 μg, 10 μg, 20 μg, 30 μg, 40 μg, 50 μg, 60 μg, 70 μg, 80 μg, 90 μg, 100 μg, 200 μg, 300 μg, 400 μg, 500 μg, 600 μg, 100 μg, 700 μg, 800 μg, 900 μg, 1 mg, 2 mg, 5 mg, 10 mg, 20 mg, 30 mg, 40 mg, 50 mg, 60 mg, 70 mg, 80 mg, 90 mg, or 100 mg (inclusive of intermediate values and ranges of values) of miltefosine in a protocol suitable for a typical adult. Miltefosine can be applied immediately (e.g. within five minutes) prior to vaccination, or can be applied from 5 minutes to 48 hours (or any suitable intervening period of time) prior to vaccination. Such a miltefosine formulation can be removed from the skin surface immediately (e.g. within five minutes) following vaccination or, alternatively, maintained on the skin surface for from 5 minutes to 48 hours following vaccination. In some embodiments the time period for pre-vaccination and/or post-vaccination topical treatment with a miltefosine formulation can be modified depending upon the age and/or immune status of the individual being treated.

In some embodiments a miltefosine-containing formulation can be applied to the skin surface at or near (e.g. within a 10 cm radius) the vaccination site and the treated skin surface covered with an occlusive dressing or similar appliance. In such embodiments an occlusive dressing can be applied following application of miltefosine formulation. Alternatively, an occlusive dressing or similar appliance can be provided that incorporates a topical miltefosine formulation on a skin-facing surface, thereby applying miltefosine formulation to the skin surface simultaneously with the application of the occlusive dressing. Such an occlusive dressing or similar appliance can include a window or similar portion that provides access to the vaccination site for purposes of injection.

In other embodiments, miltefosine can be provided in combination or as part of a vaccinating composition. Such an embodiment conveniently provides adjuvant and the vaccinating species in a single treatment.

Various objects, features, aspects and advantages of the inventive subject matter will become more apparent from the following detailed description of preferred embodiments, along with the accompanying drawing figures.

One should appreciate that the disclosed techniques provide many advantageous technical effects including simple and convenient enhancement of immune response following vaccination. Such enhancement can provide improved protection for the general population, improved vaccine effectiveness for at-risk or immunocompromised individuals, provide cross-protection against species not present in a vaccine formulation, and/or permit the use of smaller amounts of vaccinating material.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Miltefosine is an FDA-approved anti-parasitic drug that is used in the treatment of Leishmaniasis. The immunomodulating effects of miltefosine include being an agonist of TLR4 and TLR9 (Das S, Rani M, Pandey K, Sahoo G C, Rabidas V N, Singh D, et al. Combination of paromomycin and miltefosine promotes TLR4-dependent induction of antileishmanial immune response in vitro. J Antimicrob Chemother 2012; 67:2373-8; Mukherjee A K, Gupta G, Adhikari A, Majumder S, Kar Mahapatra S, Bhattacharyya Majumdar S, et al. Miltefosine triggers a strong proinflammatory cytokine response during visceral leishmaniasis: role of TLR4 and TLR9. Int Immunopharmacol 2012; 12:565-72), enhancing IFN-γ receptor (Wadhone P, Maiti M, Agarwal R, Kamat V, Martin S, Saha B. Miltefosine promotes IFN-gamma-dominated anti-leishmanial immune response. J Immunol 2009; 182:7146-54), promoting IL12-dependent TH1 response (Wadhone P, Maiti M, Agarwal R, Kamat V, Martin S, Saha B. Miltefosine promotes IFN-gamma-dominated anti-leishmanial immune response. J Immunol 2009; 182:7146-54), and inhibiting PI3K-Akt pathway (Lucas A, Kim Y, Rivera-Pabon O, Chae S, Kim D H, Kim B. Targeting the PI3K/Akt cell survival pathway to induce cell death of HIV-1 infected macrophages with alkylphospholipid compounds. PLoS One 2010; 5). Topical formulation of miltefosine has been evaluated in the treatment of breast carcinoma (Clive S, Gardiner J, Leonard R C. Miltefosine as a topical treatment for cutaneous metastases in breast carcinoma. Cancer Chemother Pharmacol 1999; 44 Suppl:S29-30). The Inventors have, surprisingly, found that miltefosine is useful as an adjuvant for seasonal influenza vaccine (using a murine model). As shown in FIG. 1, intraperitoneal miltefosine can enhance the immunogenicity of a split-virion seasonal influenza vaccine. In FIG. 1 circles indicate data from the miltefosine+vaccine treatment group, squares indicate data from the vaccine only treatment group, triangles indicate data from the miltefosine only treatment group, and inverted triangles indicate data from a saline-treated control group As shown, use of miltefosine in combination with influenza vaccination provides significantly increased IgG titer at two weeks post-immunization. Hemagglutination and microneutralization titers are also improved, showing that the enhanced IgG response is functional. It was also noted that both IgG1 and IgG2a responses were enhanced by the use of miltefosine in combination with intradermal vaccination.

Figure 2A:
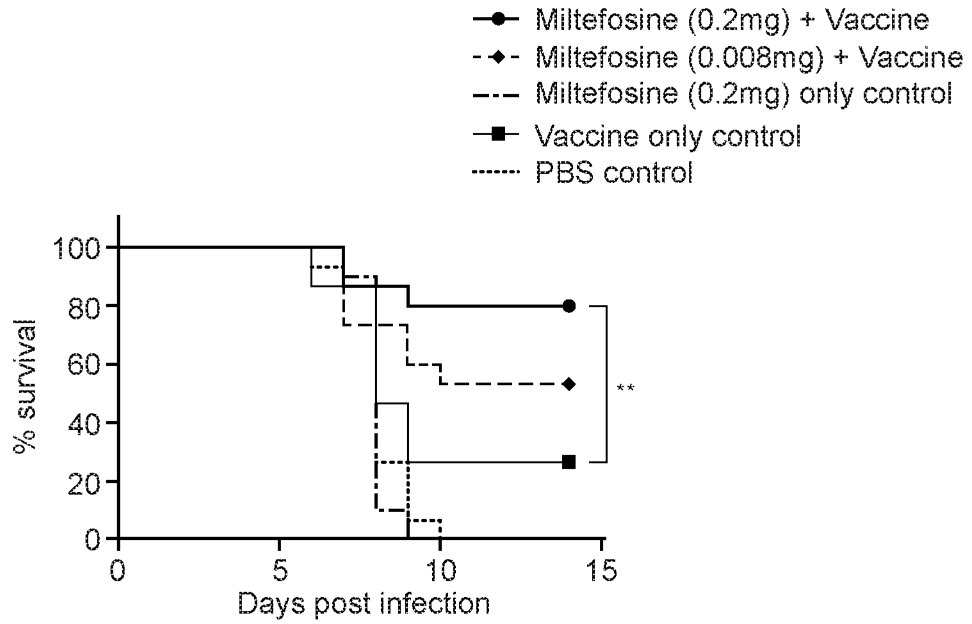
FIGS. 2A and 2B.
Figure 2B:
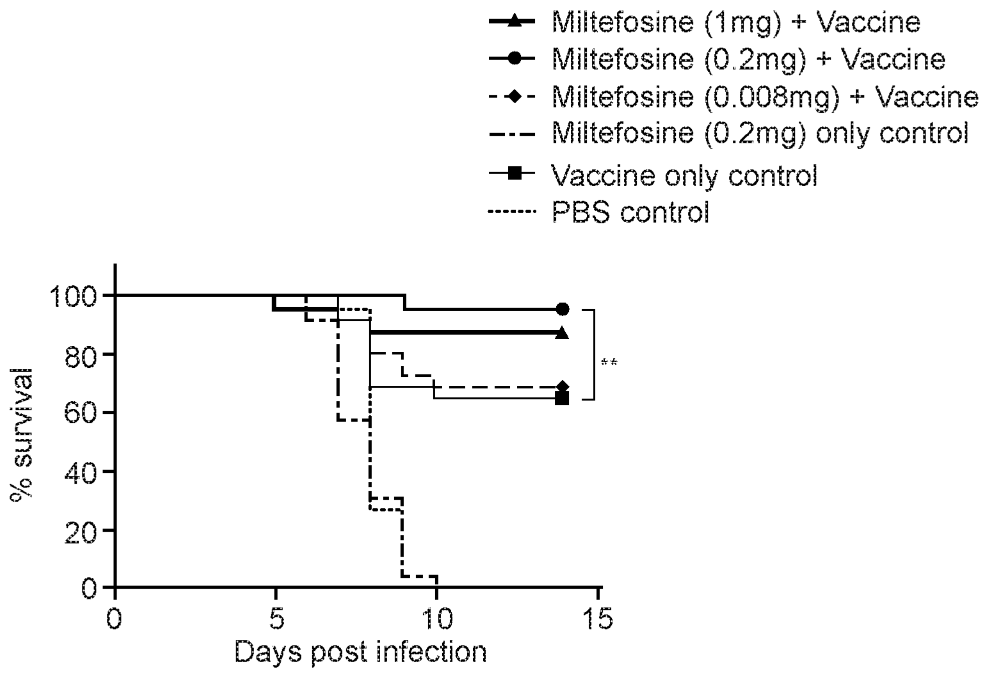

In a second series of studies mice were infected either 3 or 7 days after a single influenza vaccination. As shown in FIGS. 2A and 2B, the vaccine group receiving intraperitoneal miltefosine adjuvant showed significantly improved survival compared a vaccinated group that did not receive the adjuvant. In FIG. 2A data from treatment with 0.2 mg miltefosine+vaccine is represented by a combination a circle and a solid line, data from treatment with 0.008 mg miltefosine+vaccine is represented by a combination of a rhombus and a dashed line, data from treatment with 0.2 mg miltefosine only is represented by a dash/dot line, data from treatment with vaccine only is represented by a combination of a square and a solid line, and data from treatment with a saline control is represented by a dotted line. In FIG. 2B data from treatment with 1 mg miltefosine+vaccine is represented by a combination a triangle and a solid line, data from treatment with 0.2 mg miltefosine+vaccine is represented by a combination a circle and a solid line, data from treatment with 0.008 mg miltefosine+vaccine is represented by a combination of a rhombus and a dashed line, data from treatment with 0.2 mg miltefosine only is represented by a dash/dot line, data from treatment with vaccine only is represented by a combination of a square and a solid line., and data from treatment with a saline control is represented by a dotted line.

Figure 3:
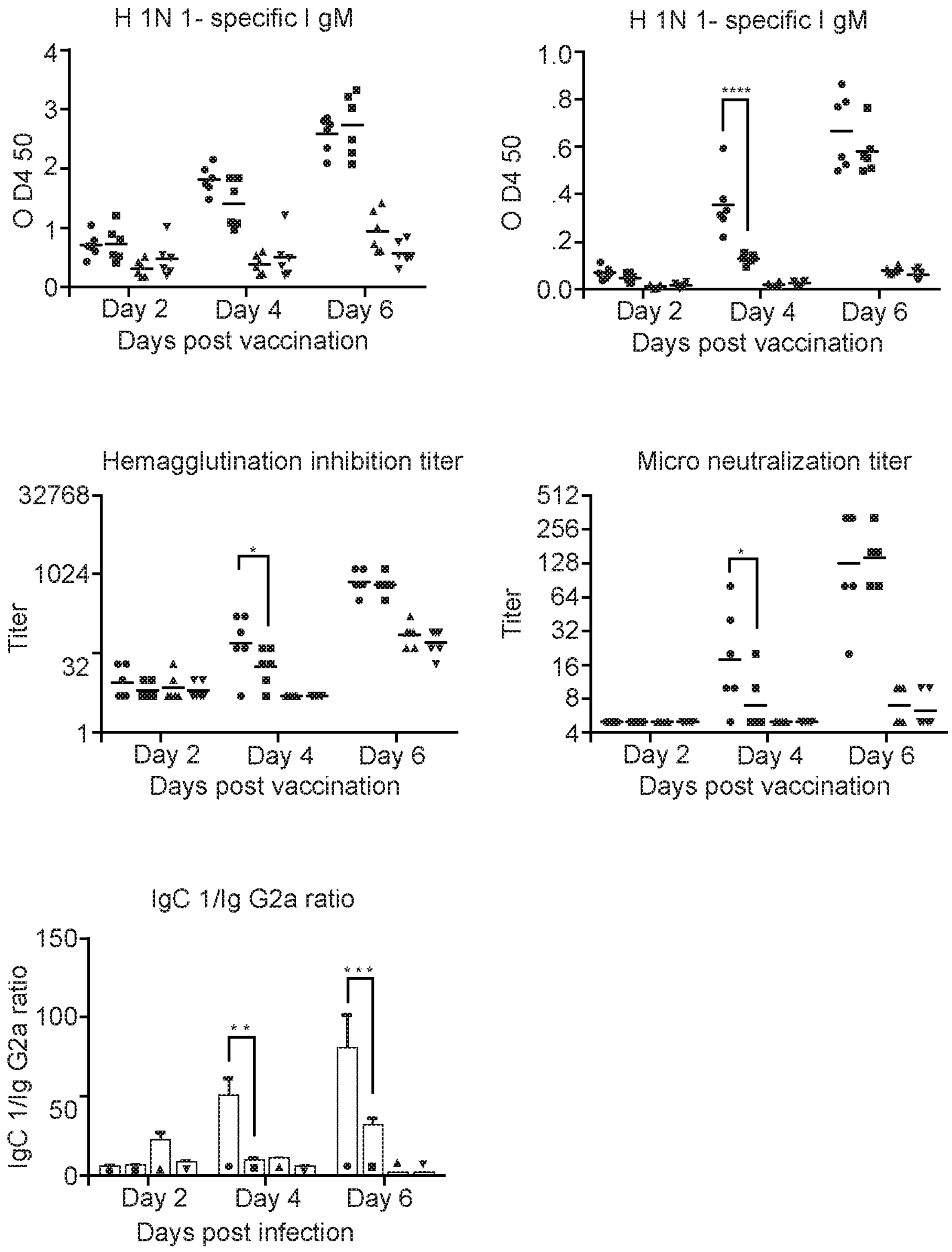
FIG. 3.

It was also found that mice receiving both an intraperitoneal miltefosine adjuvant and vaccination had significantly higher HAI and MN titers 4 days post-infection than those that received the vaccine without the adjuvant, as shown in FIG. 3. In FIG. 3 circles indicate data from the miltefosine+vaccine treatment group, squares indicate data from the vaccine only treatment group, triangles indicate data from the miltefosine only treatment group, and inverted triangles indicate data from a saline-treated control group. Since HAI and MN titer are well-established correlates for protection this result is consistent with findings in regard to survival rate (see FIGS. 2A and 2B). Surprisingly, the IgG1/IgG2 ratio for the vaccinated mice that received the intraperitoneal miltefosine adjuvant was greater than that that of the vaccine group that did not receive the adjuvant. Without wishing to be bound by theory, the Inventors believe that this suggests the group treated with both the intraperitoneal miltefosine adjuvant and the influenza vaccine exhibits a $T_H2$ biased response relative animals receiving only the vaccine.

Figure 4:
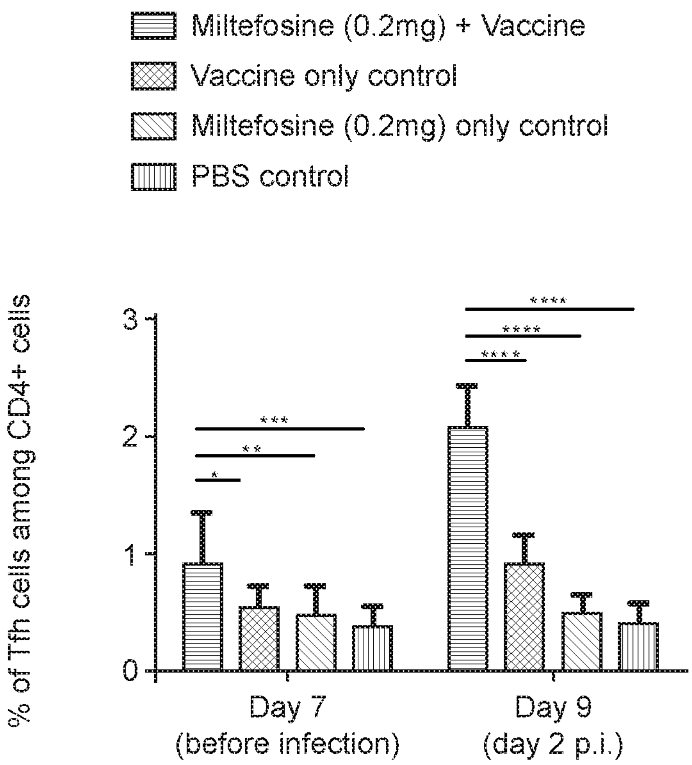
FIG. 4.

It was found that mice receiving both an intraperitoneal miltefosine adjuvant and vaccination had significantly higher percentage of splenic follicular helper T cells (Tfh) than those that received the vaccine without the adjuvant, as shown in FIG. 4. Data shown represents findings at day 7 after treatment with miltefosine and vaccine but prior to infection (left side of FIG. 4) and two days after infection (day 9, right side of FIG. 4). Without wishing to be bound by theory, the Inventors believe that this suggests the group treated with both the intraperitoneal miltefosine adjuvant and the influenza vaccine elicits better antibody response via an increase in Tfh cells.

As noted above, miltefosine can be incorporated into vaccine compositions in combination with a virus immunogen in order to provide an improved vaccine formulation. It should be appreciated that immunogens utilized in antiviral vaccines include viruses grown in cultured cells (and/or products derived from such viruses). Accordingly, another aspect of the inventive concept includes compositions and methods for increasing virus reproduction and/or yield from such cell cultures, thereby reducing the cost and complexity of immunogen production. The Inventors also consider that such methods can be utilized to realize and/or improve the sensitivity of viral diagnostic methods.

Figure 5:
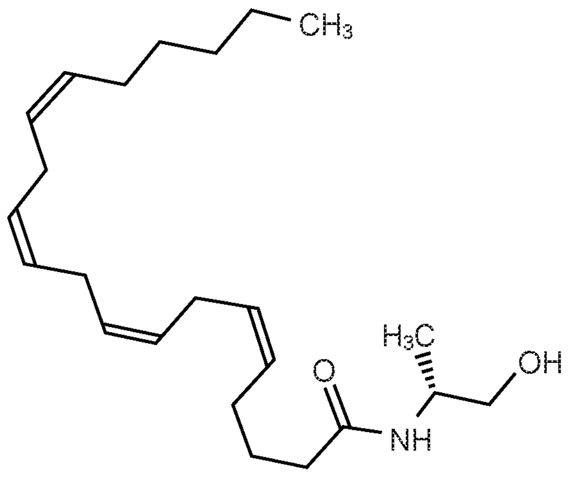
FIG. 5.

Surprisingly, the Inventors have found that the application of cannabinoid receptor agonists selected to increase lipid accumulation in cultured cells utilized for virus reproduction (e.g. hepatocytes) and applied at non-cytotoxic concentrations can result in an increased cytopathic effect on viral infection of such cultured cells. Suitable cannabinoid receptor agonists include anandamide and anandamide analogs, such as (R)-methanandamide and palmitylethanolamide. Such cytopathic effects are the result of successful viral reproduction within the cultured cells and are indicative of enhanced viral replication. The structure of (R)-methanandamide is shown in FIG. 5.

Figure 6:
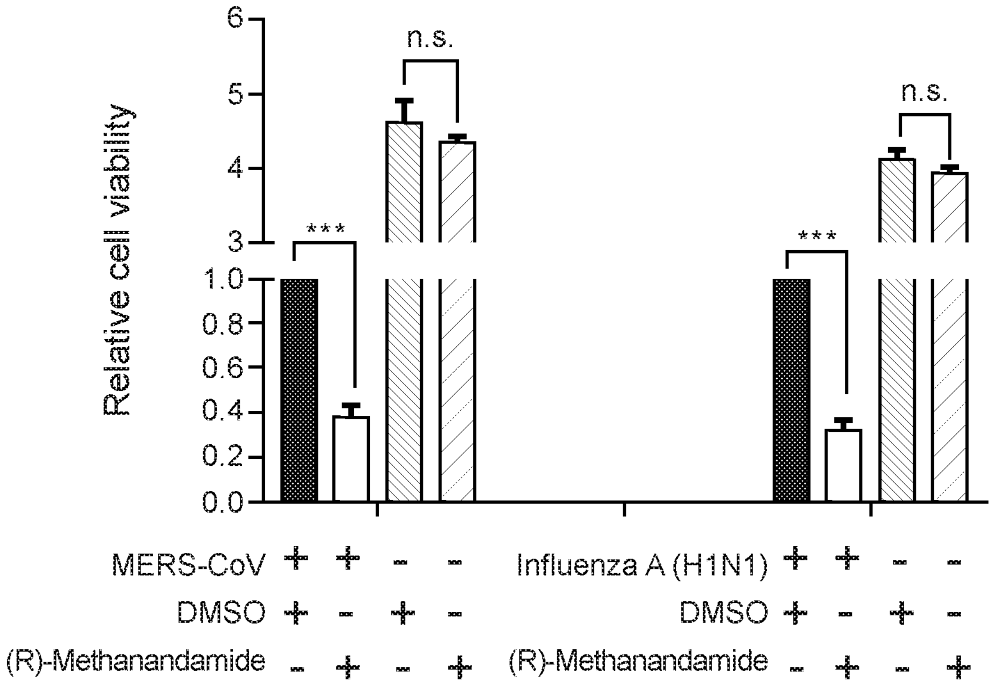
FIG. 6.

In an exemplary study, colorimetric assays reflecting cell viability were performed, in the presence of absence of (R)-methanandamide (10 μM, $CC_{50}$>60 μM), to measure cytopathic effects that developed in cultured cells upon virus infection and cytotoxicity that in the absence of virus infection. Specifically, 0.1 MOI and 24 hours post-MERS-CoV infection (Huh7 cells) and at 0.01MOI and 48 hours post-H1N1 infection (MDCK cells) were used. Cell viability was determined using an MTT assay (Invitrogen). Results are shown in FIG. 6, and are normalized by the cell-viability of virus-infected cells with DMSO treatment. The experiments were performed in triplicate. ***p<0.001 and n.s. indicates non-significant as analyzed by Student's t-test. Data are presented as mean+s.d.

Such enhanced viral replication can be used to improve virus and/or viral product yields in cell culture, thereby improving the efficiency of viral immunogen production. Such viral immunogens can be used in the formulation of antiviral vaccines (for example, preventative and/or therapeutic vaccines). In a preferred embodiment such viral immunogens are provided in combination with miltefosine in a vaccine formulation.

Another embodiment of the inventive concept is the use of a cannabinoid receptor agonist in improved assays directed to viruses. Such virus assays can be based on detection of virus, detection of viral genetic material (for example by PCR, RT-PCR, and other methodologies relying on replication of specific nucleic acids), detection of viral antigens (for example, by immunoassay, Western blot, mass spectrometry, etc.), and/or observation of cytopathic effects on cultured cells. In such methods, a sample obtained for analysis (or a virus-containing fraction of such a sample) can be introduced into cell culture in the presence of non-toxic amounts of a cannabinoid receptor agonist that causes lipid accumulation in the cultured cells (e.g. (R)-methanandamide). Enhanced viral replication results in the increased production of detectable virus markers (genetic and/or antigenic), permitting earlier and/or more sensitive detection than in the absence of the cannabinoid receptor agonist, and also results in increased cytopathic effects that are directly observable.

Such cell culture steps need not be performed to the point of cell lysis or observable cytopathic effect, but rather can be performed for a period of time sufficient to result in replication of virus or identifiable viral components within the cell. In methods employing such abbreviated incubation periods cells in culture can be lysed (for example, by grinding, sonication, addition of surfactant, osmotic shock, etc.) to release virus and/or viral products for subsequent detection. In some embodiments rapid diagnostic methods (for example, real time PCR, a flow immunoassay, a point of care test, etc.) can be utilized in such cell-based assays or methods to provide a rapid diagnostic method with improved sensitivity and advantageously having improved specificity accorded by specific interactions between the virus and the cultured cells.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method for improving an immune response to an influenza virus, comprising:

administering an adjuvant comprising miltefosine to a subject at or near a site of vaccination on the subject; and introducing an influenza vaccine at the vaccination site, the influenza vaccine comprising a vaccinating influenza species, wherein the adjuvant is selected to provide miltefosine in a quantity sufficient to increase the immune response relative to a vaccinated subject that has not been administered the adjuvant;

wherein the adjuvant comprising miltefosine is administered immediately prior to vaccination or from about 5 minutes to about 48 hours prior to vaccination; and wherein the adjuvant comprising miltefosine is administered by intramuscular injection, intradermal injection, or topical application.

2. The method of claim 1, wherein the immune response is selected from the group consisting of an increased IgG titer, an increased IgM titer, an increased hemagglutination inhibition titer, and an increased microneutralization titer.

3. The method of claim 1, wherein the adjuvant is applied topically over the vaccination site as a topical formulation, and further comprising the step of applying a barrier over the vaccination site.

4. The method of claim 1, wherein the adjuvant delivers from 1 μg to 100 mg of miltefosine.

5. The method of claim 1, wherein the vaccine comprises a multivalent influenza vaccine.

6. The method of claim 5, wherein the multivalent influenza vaccine is a trivalent influenza vaccine.

7. The method of claim 1, wherein the influenza vaccine is administered via intramuscular, intradermal, or intraperitoneal injection.

8. The method of claim 1, wherein the adjuvant comprising miltefosine is applied about 5 minutes prior to vaccination.

9. The method of claim 3, wherein the topical formulation comprises part of an application device.

10. The method of claim 1, wherein the adjuvant is selected to deliver miltefosine in a quantity sufficient to increase an antibody titer to the vaccinating influenza species, relative to an antibody titer generated on vaccination without administration of the adjuvant.

11. The method of claim 1, wherein the adjuvant is provided in a pharmaceutically acceptable carrier.

12. The method of claim 1, wherein the adjuvant is removed from the vaccination site following vaccination.

13. The method of claim 12, wherein the adjuvant is removed from the vaccination site immediately following vaccination or about 5 minutes to about 48 hours following vaccination.

14. The method of claim 7, wherein the influenza vaccine is administered via intradermal injection.

15. The method of claim 1, wherein the adjuvant provides 6% miltefosine.

* * * * *